United States Patent [19]
Lambers et al.

[11] Patent Number: 5,693,677
[45] Date of Patent: Dec. 2, 1997

[54] CERAMIDE 3 DERIVATIVES BASED ON MONOUNSATURATED FATTY ACIDS

[75] Inventors: Johannes Wilhelmus Jacobus Lambers, Pijnacker; Jan Verweij, Leiden, both of Netherlands

[73] Assignee: Gist-brocades N.V., Netherlands

[21] Appl. No.: 647,980

[22] PCT Filed: Oct. 2, 1995

[86] PCT No.: PCT/EP95/03908

§ 371 Date: May 30, 1996

§ 102(e) Date: May 30, 1996

[87] PCT Pub. No.: WO96/10557

PCT Pub. Date: Apr. 11, 1996

[30] Foreign Application Priority Data

Sep. 30, 1994 [NL] Netherlands ............ 94202836.6

[51] Int. Cl.[6] .................................................. A61K 6/00
[52] U.S. Cl. ........................... 514/844; 424/401; 514/847
[58] Field of Search ............................ 424/401; 514/844, 514/847

[56] References Cited

U.S. PATENT DOCUMENTS 5,368,857  11/1994  Corcoran et al. .

FOREIGN PATENT DOCUMENTS

| 0 227 994 | 7/1987 | European Pat. Off. . |
| 0 282 816 | 9/1988 | European Pat. Off. . |
| 0 600 437 | 8/1992 | European Pat. Off. . |
| 0 662 319 | 7/1995 | European Pat. Off. . |
| WO 95/11881 | 5/1995 | WIPO . |
| WO 95/25716 | 9/1995 | WIPO . |

OTHER PUBLICATIONS

Fulmer, A.W., et al., *J. of Investigative Dermatology, Inc.*, (1986) 86:598–602.
Kraus, R. et al., *Liebigs Ann. Chem.*, (1991) 1991:125–128.
Long, S.A., et al., *Arch Dermatol Res.*, (1985) 277:284–287.
Wertz, P.W., et al., *J. or Investigative Dermatology*, (1985) 84:410–412.
Wertz, P.W. et al., *J. of Lipid Res.*, (1983) 24:759–765.
Derwent WPI, Derwent Abstract No. AN 93–070179 (Kao Corp.) (1993).
Vedanayagam, H.S., et al., "Preparation, characterization and surfactant properties of fatty acid diethanolamides" *J. Oil Technol. Assoc. of India* (1984) 15:68–71.

Primary Examiner—Terressa M. Mosley
Attorney, Agent, or Firm—Morrison & Foerster LLP

[57] ABSTRACT

The present invention discloses ceramide 3 derivatives based on monounsaturated fatty acids. A preferred compound is N-oleoylphytosphingosine (Ceramide IIIB). A method for preparing these compounds is also disclosed. The solubility of these compounds is higher than the solubility of the corresponding saturated ceramide 3 derivatives, whereas their stability is comparable to saturated ceramide 3 stabilities. In addition, a method is described for maintaining the water permeability characteristics of the skin by topical application of a formulation containing a monounsaturated ceramide 3 derivative.

31 Claims, 6 Drawing Sheets

CERAMIDE 3 DERIVATIVES BASED ON MONOUNSATURATED FATTY ACIDS

TECHNICAL FIELD

The present invention relates to new physiologically active ceramide derivatives. Specifically, the invention relates to new ceramide 3 derivatives based on monounsaturated fatty acids. These ceramide 3 derivatives are soluble in normally employed ceramide solvents and have a relatively high oxidation stability. The bioavailability is increased and the ceramide is used for maintaining the epidermal water permeability barrier of the skin.

BACKGROUND OF THE INVENTION

It is generally understood that ceramides present within the intercellular lipid lamellae of the stratum corneum have an important structural function in the water permeability barrier of the skin. The ceramides are considered essential in structuring and maintaining said barrier. It is believed that one of the causes of dry skin is a reduction in the amount of ceramides within these intercellular lipid lamellae. It is therefore desirable to be able to successfully replace these depleted lipida via the topical route.

Downing et al. (Arch. Dermatol. Res. 277, 284–287, 1985; J. Invest. Derm. 84, 410–412, 1985; J. Lipid Res. 24, 759–765, 1983) identified the six predominant existing types of ceramides in the stratum corneum. It is observed that in surfactant-induced dry skin there exists a relative deficiency of a ceramide with phytosphingosine as a backbone (A. W. Fulmer et al. J. Invest. Derm. 86, 598–602, 1985). This ceramide was identified by Downing as ceramide 3. Ceramide 3 is a mixture of different molecules, characterized by the general name N-acylphytosphingosine, wherein the acyl group is saturated and has a chain length of 14 to 30 carbon atoms.

Ceramides must be able to penetrate the stratum corneum in order to reach the lipid lamellae of the permeability barrier. One of the unsolved problems with the topical application of skin products is to find a suitable way to deliver the active ingredient in sufficient amounts to the place where it must exert its biological activity. The penetration of the ceramides in the skin is highly dependent on their solubility in a cosmetic formulation.

KAO has disclosed in the European Patent Applications, EP 227994 and EP 282816 that surfactants such as glycerylethers assist in penetration of ceramides into the stratum corneum. However, these kind of surfactants tend to permanently disrupt the stratum corneum so that afterwards the penetrated ceramide leaks out of the stratum corneum again.

A class of compounds with well known surfactant properties are fatty acids via acylation coupled with the aminoalcohol diethanolamine. It is observed that the surfactant properties of these compounds improve with increasing degree of unsaturation of the fatty acyl group. (H .S. Vedanayagam et al., J. Oil Technol. Assoc. India, 15, 68–71, 1984).

In ceramide 3, a saturated fatty acid ($C_{14}$–$C_{30}$) is coupled via acylation with phytosphingosine. Although phytosphingosine also is an aminoalcohol, it is structurally very different from diethanolamine. In contrast to diethanolamine, phytosphingosine already contains an alkyl chain (having a length of 14 carbon atoms in ceramide 3). The influence of the presence of this phytosphingosine alkyl chain on modifications in the acyl group of ceramide 3 therefore cannot be predicted.

SUMMARY OF THE INVENTION

The invention provides novel compounds having the following formula:

wherein R is a straight chain or branched alkyl group containing one double bona and having up to 55 carbon atoms, preferably 10 to 50 carbon atoms, more preferably 14 to 48 carbon atoms, and X is an integer from 11 to 21, inclusive, preferably 13.

A preferred compound of the present invention is N-oleoyl phytosphingosine.

The invention further provides a method for preparing a monounsaturated derivative of ceramide 3 by the acylation of phytosphingosine with monounsaturated fatty acids.

The compounds of the present invention are soluble in fatty alcohol containing solvents, their solubility being higher than that of corresponding ceramide 3 derivatives containing saturated acyl groups.

In addition, it is described that the compounds of the present invention have a stability which is comparable to the stability of saturated ceramide 3 derivatives.

The compounds of the present invention are used in therapy or in cosmetics.

Compositions containing the new compounds are used for restoring and/or maintaining the integrity of the epidermal water permeability barrier of the skin.

The present invention discloses a method for restoring and/or maintaining the water permeability characteristics of the skin, characterized in that a formulation containing a compound of the present invention is applied topically.

DETAILED DESCRIPTION OF THE INVENTION

Figure 1:
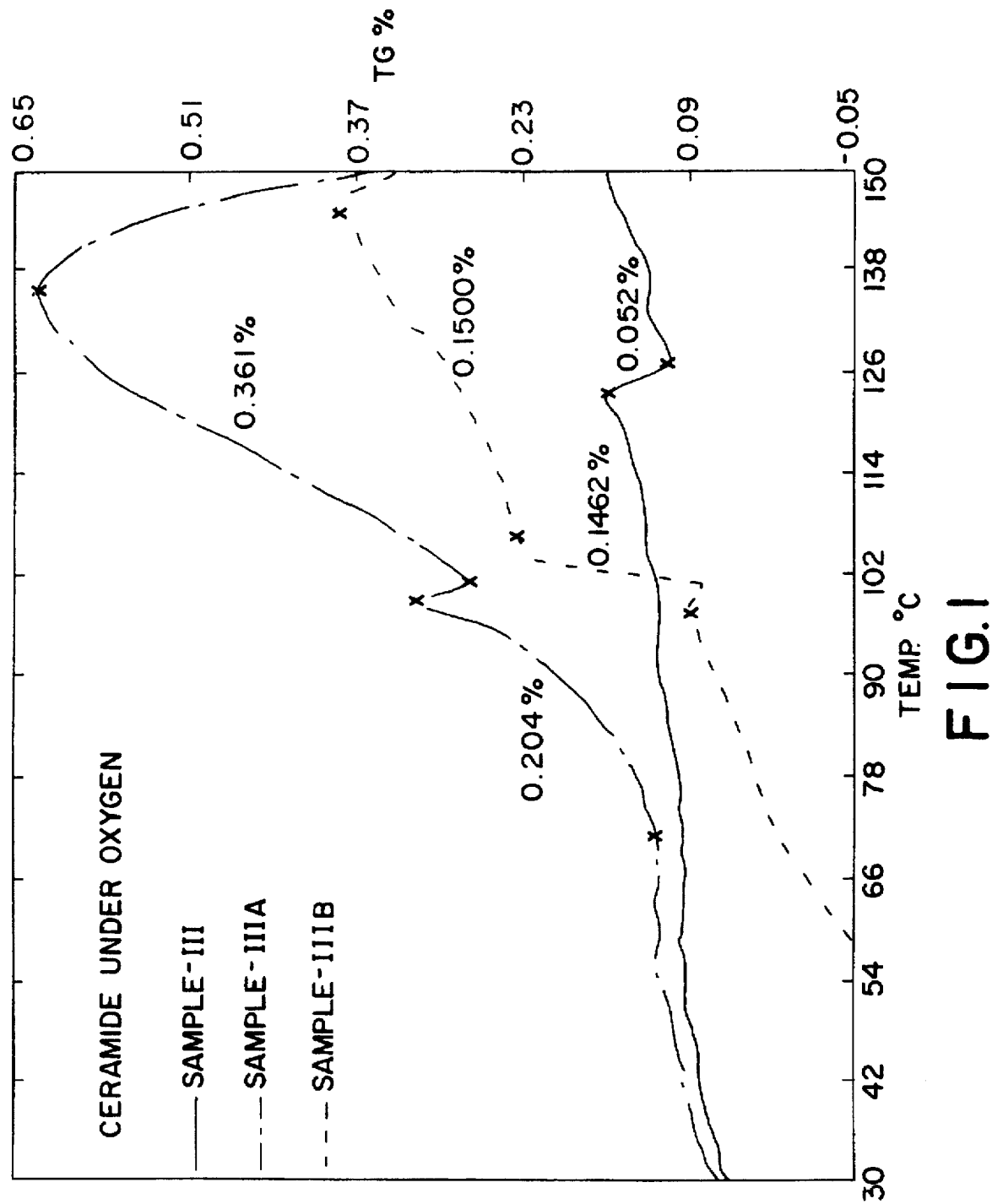
FIG. 1 is a TG scan of N-stearoylphytosphingosine (sample III), N-oleoylphytosphingoside (sample IIIB) and N-linoleoylphytosphingosine (sample IIIA).

The present invention provides novel compounds having the following formula:

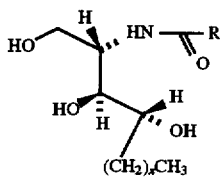

wherein R is a straight chain or branched alkyl group containing one double bond and having up to 55 carbon atoms, preferably 10 to 50 carbon atoms, more preferably 14 to 48 carbon atoms, and X is an integer from 11 to 21, inclusive, preferably 13.

The compounds of the present invention are ceramide 3 derivatives in which phytosphingosine is acylated with a monounsaturated fatty acid (so-called monounsaturated ceramide 3 derivatives).

A preferred compound of the present invention is N-oleoyl phytosphingosine.

Natural ceramide 3 also has a phytosphingosine backbone; however, in this molecule the phytosphingosine is acylated with saturated fatty acids (so-called saturated ceramide 3 compounds).

The invention further provides a method for preparing monounsaturated ceramide 3 derivatives. These derivatives may be prepared by various synthesis methods known to the skilled person, the choice of the synthesis method being not critical to the present invention.

The coupling between a monounsaturated fatty acid and phytosphingosine or a salt thereof can be carried out either enzymatically or chemically, whereby the choice of the monounsaturated fatty acid is made such that its acyl group corresponds to the type of acyl chain which is desired in the monounsatureated ceramide 3 derivative. Chemically, an appropriate fatty acid can be coupled either as such using coupling reagents, e.g. EEDQ (N-ethoxycarbonyl-2-ethoxy-1,2-dihydroquinoline), HOBT (hydroxybenzotriazole) or a carbodiimide, or as an activated acid e.g. a mixed anhydride or acid halogenide.

An example of a chemical synthesis method is a method analogous to that of Mori and Nishio (1991) Liebigs Ann. Chem., 253–257.

Phytosphingosine is obtainable efficiently by deacetylation of tetra-acetylphytosphingosine (TAPS), which on its turn can be obtained in large amounts by microbial fermentation, especially by fermentation of Pichia ciferri.

In another aspect of the invention it is disclosed that the new compound of the present invention is highly soluble in solvents containing fatty alcohol, esters, triglycerides and fatty acids, which can be used as emollients and which are accepted for use on the human skin. Examples of such solvents are: lauryl alcohol, cetyl alcohol, isocetyl alcohol, oleyl alcohol, stearoyl alcohol, isostearoyl alcohol, isopropyl myristate, isopropyl stearate, cetyl palmitate, sugar- and glycol esters, triglycerides such as plant derived oils and capric/caprylic triglyceride and fatty acids such as palmitic, stearic and isostearic acid.

It is shown that a saturated ceramide 3 compound with an acyl group of 18 carbon atoms can be solubilised in isocetyl alcohol, isostearic acid and various oils, in an amount of less than 0.2% (w/v). In contrast, the monounsaturated ceramide 3 derivatives of the present invention solubilise to a considerably higher extent in the indicated solvents.

It is further shown that the stability of the monounsaturated ceramide 3 derivatives of the present invention is comparable to that of their saturated counterparts, whereas monounsaturated ceramide 3 derivatives have a higher stability than their corresponding diunsaturated ceramide 3 derivatives.

The compounds of the present invention are used in therapy or in cosmetics. Specifically, the ceramide 3 derivatives of the invention are used for restoring and/or maintaining the integrity of the epidermal water permeability barrier of the skin. Also, these ceramide 3 derivatives, like ceramides in general, can be used as important regulators of cell differentiation and cell proliferation (R. Kolesnick and Z. Fuks, J. Exp. Med. 181, 1949–1952, 1995).

Specific cosmetic compositions include the usual components. The composition comprises a vehicle to enable the active ingredient to be conveyed to the skin. Vehicles include water, solids and liquids. These are classified as emollients, propellants, solvents, humectants, thickeners and powders.

Emollients include alkyl higher fatty acids, oils, esters, higher alcohols.

Propellants include propane, butane, isobutane, dimethyl ether, chlorofluoroalkanes, carbon dioxide, nitrous oxide.

Solvents include ethyl alcohol, methylene chloride, isopropanol, ethyl ethers, DMSO, propylene glycol, butylene glycol.

Humectants include gelatin, polyols such as glycerin, sorbitol.

Powders include chalk, talc, starch, gums.

The vehicle additionally contains specific agents that are able to interact with the stratum corneum to alter its natural resistance, the so-called penetration enhancers. The present invention describes specific formulations which are able to target the ceramide to the proper site in the skin, i.e. the stratum corneum. The skin penetration enhancers should be present in the formulation to ensure proper targeting and, consequently, high efficacy of the ceramides. Various compounds can display a function as penetration enhancer, e.g. solvents and amphiphilic (surface active) compounds. Penetration enhancers include ethoxylated emulsifiers, such as Ceteareth-6 or Ceteareth-25.

The skin penetration enhancers further may be used in combination with an oil, such as a vegetable oil containing relatively high concentrations of oleic acid.

The combination of the said components can account for 10 to 99% of the composition.

The compositions containing the monounsaturated ceramide 3 derivatives of the present invention are suitable for topical use. The amount of ceramide suitable for topical application ranges from 0.0001% to 25%, preferably from 0.005% to 5%, most preferably from 0.01 to 2% by weight of the composition.

The present invention discloses a method for restoring and/or maintaining the water permeability characteristics of the skin, characterized in that a formulation containing a monounsaturated ceramide 3 derivative is applied topically.

By topical application of a monounsaturated ceramide 3 derivative, e.g. N-oleoyl phytosphingosine, on skin pretreated with a surfactant (e.g. sodium dodecyl sulphate or SDS), it is shown that this ceramide has a high capacity for recovering diminished water-retaining properties of the skin, in other words for restoration of the impaired lipid barrier of the skin. In addition, it is shown that a pretreatment of the skin with compositions containing a monounsaturated ceramide 3 derivative protects the skin against SDS-induced skin damage. These ceramides further have a clear moisture-retaining effect on healthy skin.

The present invention is illustrated by several examples which in no way are intended to limit the scope of the invention.

EXPERIMENTAL

Measurement Equipment

Skin Humidity

The corneometer CM 820 PC (Courage and Khazaka, Cologne, Germany) registers the electrical capacitance of the skin surface, which is a measure of the degree of moisture on the skin's surface. The capacitance is expressed digitally in arbitrary units (a.u.). Three measurements were performed on each test area and the mean was used to define hydration state of the stratum corneum.

The corneometer comprises a console and its sensor. The sensor is connected to the console by a special plug and coiled cable. The measurement is indicated on the 40×18 mm display screen on the console as a three-place number. The display also fulfils other information functions.

The sensor is rectangular in shape. Its special glass coated active front surface can be moved axially, and has a stroke of at least 3 mm. The measuring principle demands that the sensor surface be placed flat on the test object at a constant pressure. In order to ensure this as reproducibly as possible, the front surface of the measuring head has been designed to be very small (7×7 mm). The inner moveable part —the active front surface—is pressed against the skin by a spring using a force of 3.5N.

The corneometer is completely automatic in operation. In-order to carry out a measurement, the measuring head is pressed against the area of skin to be measured. The measured value is displayed after one second.

Trans-epidermal Water Loss

Measurements of trans-epidermal water loss (TEWL) were performed with the Tewameter (Courage & Khazaka, Cologne, Germany). The Tewameter is a device for measurement of water evaporation on skin surfaces based on the diffusion principle discovered by A. Fick in 1885.

Skin Colour

Skin colour was measured by chromametry with a Minolta Chromameter CR 300 (Minolta, Ahrensburg, Germany) in compliance with the Commission International de l'eclairage (CIE) system, according to which the registration of colour is adjusted to the non-linear colour sensitivity of human eye. A colour is expressed in a three-dimensional coordinate system with green-red (a*), yellow-blue (b*) and L* axes (brightness). The skin surface is illuminated by a Xenon flash light and remitted light registered and analysed by a photoreceiver. Chromametry is sensitive and accurate for the characterization of redness of skin irritation. In inflamed skin a positive change on the a, axis is observed, towards red. Each value was the average of three recordings.

Statistics

Summary statistics (Statgraphics Plus Version 6, Manugistics U.S.A.) procedure was used to determine the center, spread, and shape of the data. The system performs the following calculations: average, median, variance, standard deviation, standard error, minimum and maximum.

EXAMPLE 1

A Method For Preparing N-oleoylphytosphingosine

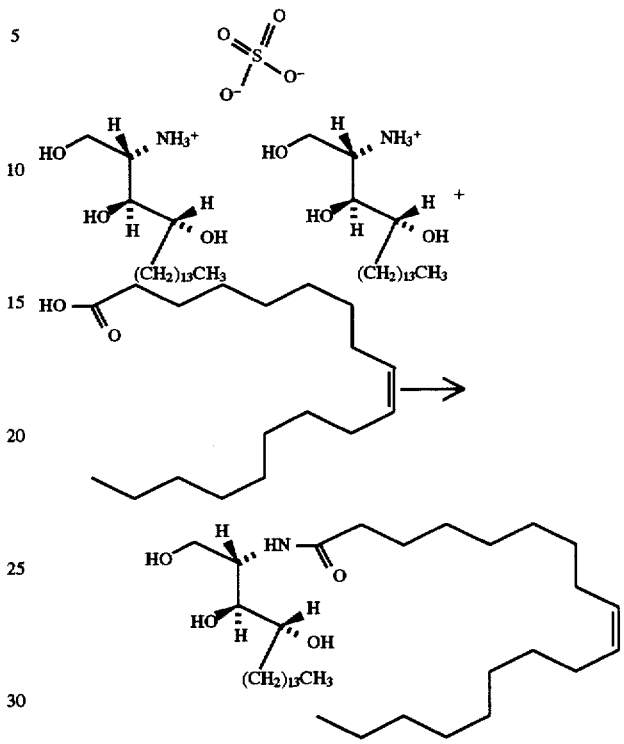

To a mixture of p-toluenesulfonyl chloride (54.43 g; 286 mmoles) and ethyl acetate (425 ml) stirred at 40° C. a solution of oleic acid (86.1 g; purity 90%; 305 mmoles) and triethyl amine (100 ml) in ethyl acetate (160 ml) was added during 30 minutes. After stirring was continued at 43° C. for another 30 minutes this reaction mixture, containing the mixed anhydride of oleic acid, was added to a stirred mixture of phytosphingosine sulphate (84.03 g), triethyl amine (40 ml) and ethyl acetate (275 ml) during 30 minutes at 43° C. The flask that contained the mixed anhydride was rinsed with 50 ml ethyl acetate. After stirring for about 1 hour at 43° C. 400 ml of water was added to the reaction mixture and the pH was adjusted at 6.8 with 18 ml of a HCl solution (37%). The the layers were separated and the organic layer was washed again with 400 ml of water of which the pH was adjusted to 6.4 with 2 ml of a HCl solution (37%). After washing the ethyl acetate layer with 150 ml of a NaCl solution (10% in water) 500 ml of ethyl acetate was removed by distillation. More ethyl acetate (500 ml) was added and another 200 ml of ethyl acetate was removed by distillation. After cooling the ethyl acetate solution to 20° C. the crystalline product was filtered off, washed with ethyl acetate (2×200 ml) and dried in vacuo giving 87.99 g of N-oleoyl-phytosphingosine.

PMR-spectrum (360 MHz; $CDCl_3/CD_3OD$ v/v 1:1); values in ppm; δ $CH_3OH$ 3.3).

δ: 0.84 (t, 3H,); 1.1–1.7 (m, 48H); 1.97 (m, 4H); 2.18 (t, 2H); 3.52 (m, 2H); 3.71 (dABq, 2H); 4.06 (m, 1H); 5.30 (m, 2H).

EXAMPLE 2

Solubility of the N-oleoylphytosphingosine

The compound produced in Example 1, N-oleoyl phytosphingosine (also called Ceramide IIIB) was tested by solubilisation in isocetyl alcohol (Eutanol™ G16, Henkel), isostearic acid (Emersol, Henkel), triglycerides (Myritolo 318, J. Dekker), wallnut oil (J. Dekker) and avocado oil (J. Dekker).

Increasing amounts of the compound were added to the solvent and stirred under nitrogen for 30 minutes at 45° C. After cooling to room temperature (22° C.±2° C.) the solutions were kept in the dark. After 1, 24 and 48 hours the solutions were visually inspected. The maximum concentration was determined before the solution turned cloudy, indicating the presence of insoluble crystals.

The solubility of a saturated ceramide 3 derivative, N-stearoylphytosphingosine, was also determined. Results are shown in Table 1. It can be seen that N-oleoyl phytosphingosine solubilizes much better than its saturated analogue.

The solubility can be further enhanced by the addition of 5–50% ethanol, propylene glycol or butylene glycol.

TABLE 1

| Solubility of ceramide 3 derivatives (% w/v). | | |
|---|---|---|
| EMOLLIENT | CERAMIDE III | CERAMIDE IIIB |
| Eutanol G16 | 0.16 | 1.2 |
| Emersol | 0.06 | 0.8 |
| Myritol 318 | 0.005 | 0.08 |
| wallnut oil | 0.005 | 0.02 |
| avocado oil | 0.005 | <0.02 |

Ceramide III N-stearoylphytosphingosine
Ceramide IIIB N-oleoylphytosphingosine

EXAMPLE 3

Thermo-gravimetric Analysis of Ceramides

Thermo-gravimetry (TG) and Differential Thermo-gravimetric Analysis (DTA) were carried out using the SSC 5200 system of Seiko, provided with the TG/DTA furnaces. Standard procedures were used to obtain the desired data.

| Settings TG/DTA: | |
|---|---|
| Temperature programme | 25° to 180° C. |
| Heating rate | 5° C./min |
| Sampling | 0.5 sec |
| Atmosphere | oxygen (100 ml/min) |
| Reference | empty, open Pt pan |
| Sample size | ± 5 mg powder |
| Sample container | open Pt pan |

The analysis shows (see FIG. 1) that the saturated ceramide 3 (N-stearoylphytosphingosine, sample III) is the most stable compound as is illustrated by the absence of change of weight. The monounsaturated N-oleoylphytospingosine (sample IIIB) has a behaviour similar to ceramide 3, although showing a steadily increasing baseline, probably due to hydration. However, no sudden increase in weight followed by decomposition is observed. A diunsaturated ceramide 3 derivative, N-linoleoylphytosphingosine (sample IIIA) shows an increase in weight (oxidation) followed by decomposition, these phenomena are very pronounced and start already at ca. 80° C.

EXAMPLE 4

Long-term Effects of Ceramide IIIB on Healthy Skin

| Formulations tested | | |
|---|---|---|
| | O/W-Emulsion with Ceramide IIIB | Placebo |
| Ceteareth-6 (and) stearyl alcohol | 3.25 | 3.25 | 3.25 |
| Ceteareth-25 | 1.75 | 1.75 | 1.75 |
| Caprylic/capric triglyceride | 3.00 | 3.00 | 3.00 |
| Stearyl Beeswaxate | 1.00 | 1.00 | 1.00 |
| Decalyceryl pentaisostearate | 5.00 | 5.00 | 5.00 |
| Cetyl alcohol | 2.50 | 2.50 | 2.50 |
| Avocado Oil | 5.00 | 5.00 | 5.00 |
| Octyl stearate | 2.00 | 2.00 | 2.00 |
| Dioctylcyclohexane | 3.00 | 3.00 | 3.00 |
| Ceramide IIIB | 0.50 | 0.20 | 0.00 |
| Preservative* | 0.50 | 0.50 | 0.50 |
| Water | 72.50 | 72.80 | 73.00 |
| Total | 100.00 | 100.00 | 100.00 |

*Propylene glycol (and) phenoxyethanol (and) methylparaben (and) propylparaben (and) ethylparaben (and) butylparaben Time of Evaluation before treatment
2 hours after last application on days 7, 14, 28
two and four days after application was ceased Test Method Five female volunteers at the age of 28–40 years with healthy skin were included in the test.

Measurements were carried out at a temperature of 22°±1° C. and a relative humidity of 60±10%. Subjects were accustomed to ambient conditions for 20 min prior to any measurement. The test was carried out on the volar forearms. Initially untreated skin was measured in all three areas to find baseline values. After measuring the three test products were applied, one area remained Entreated. The dose of application was about 2 mg/cm$^2$. In the following 28 days a home application in the morning and evening took place.

Measurements were evaluated during the treatment period on day 7, 14 and 28 two hours after the last daily application. The application was ceased on day 28 and further measurements were evaluated on day 30 and 32. Use of other cosmetic products was restricted on the test areas throughout the whole study.

Results

Figure 2:
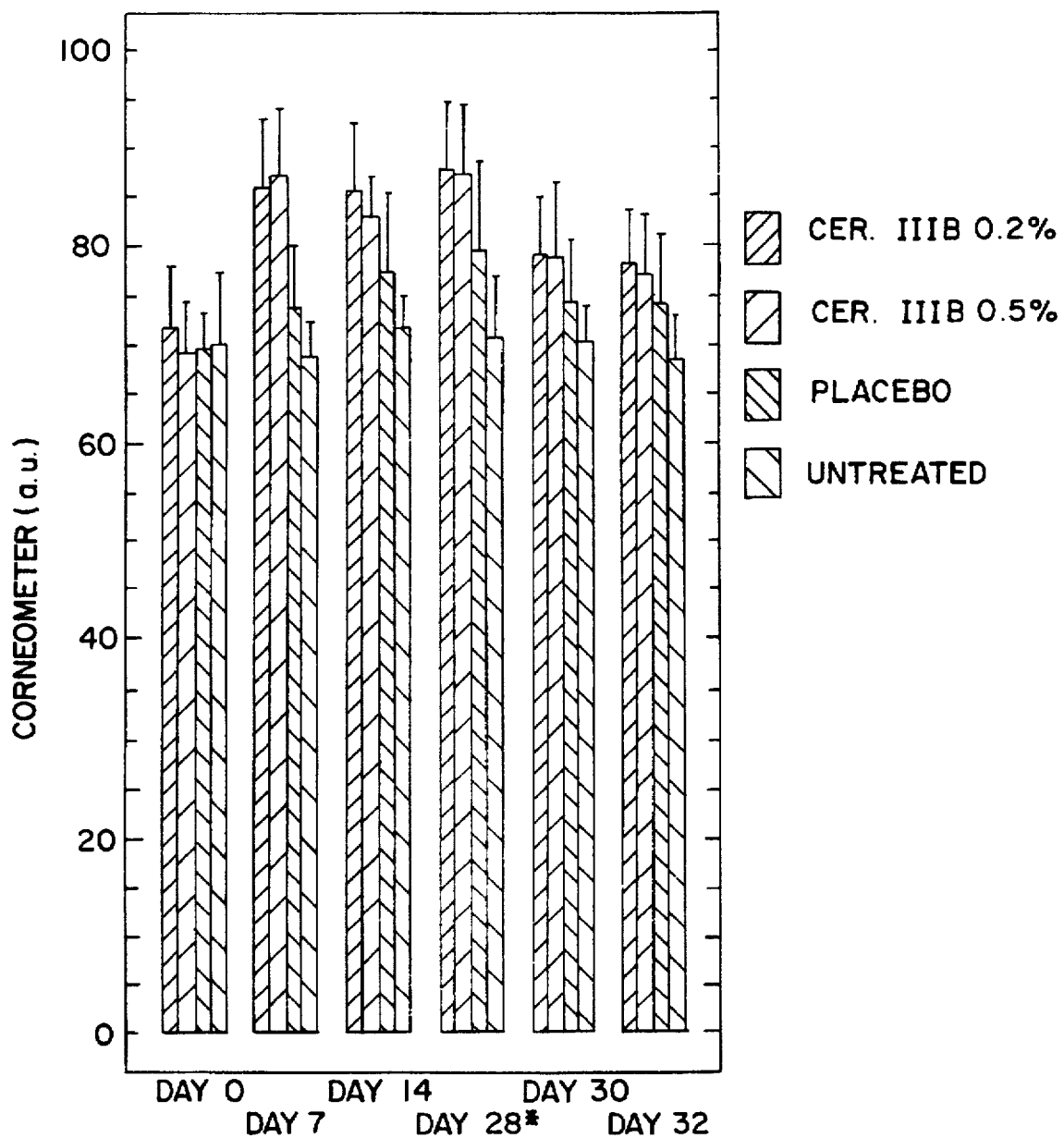
FIG. 2 shows the effects of ceramide IIIB formulations off healthy skin as measured with corneometry.

FIG. 2 shows the mean results of skin humidity measurements plus standard deviation in barcharts. The ceramide containing creams (0.2%, 0.5%) gave clear effects compared to placebo. With two daily applications the maximal effect was achieved after around 14 days and then remained nearly constant throughout the further application period. Two and four days after the last application the humidity of the skin was still significantly increased compared to placebo and untreated area.

Conclusion

The ceramide containing products gave clear moisturizing effects compared to placebo.

Thus, the effect of ceramide containing preparations in enhancing the properties of the stratum corneum with respect to its water retaining function is proved in this example.

EXAMPLE 5

Effects of Ceramide IIIB on SDS-damaged Skin

Formulations Tested

See Example 4.

Time of Evaluation after damaging the skin with SDS
1 hour after last application on days 3, 7, 14

Test Method

Five female volunteers at the age of 22–43 years with healthy skin were included in the test.

Measurements were carried out at a temperature of 22°±1° C. and a relative humidity of 60±10%. Subjects were accustomed to ambient conditions for 20 min prior to any measurement. The test was carried out on the volar forearms. The skin of the forearms was treated with a 5% aqueous solution of sodium lauryl sulphate (SDS) and an occlusive dressing applied. The dressing was removed 2 h later, and the regions gently washed with water and air-dried. After 30 min the measurements were done. Then the three test products were applied, one area remained untreated. The dose of application was about 2 mg/cm². In the following 14 days a home application in the morning and evening took place.

Measurements were evaluated during the treatment period on day 3, 7 and 14 one hour after the last daily application. Use of other cosmetic products was restricted on the test areas throughout the whole study.

Results

Figure 3:
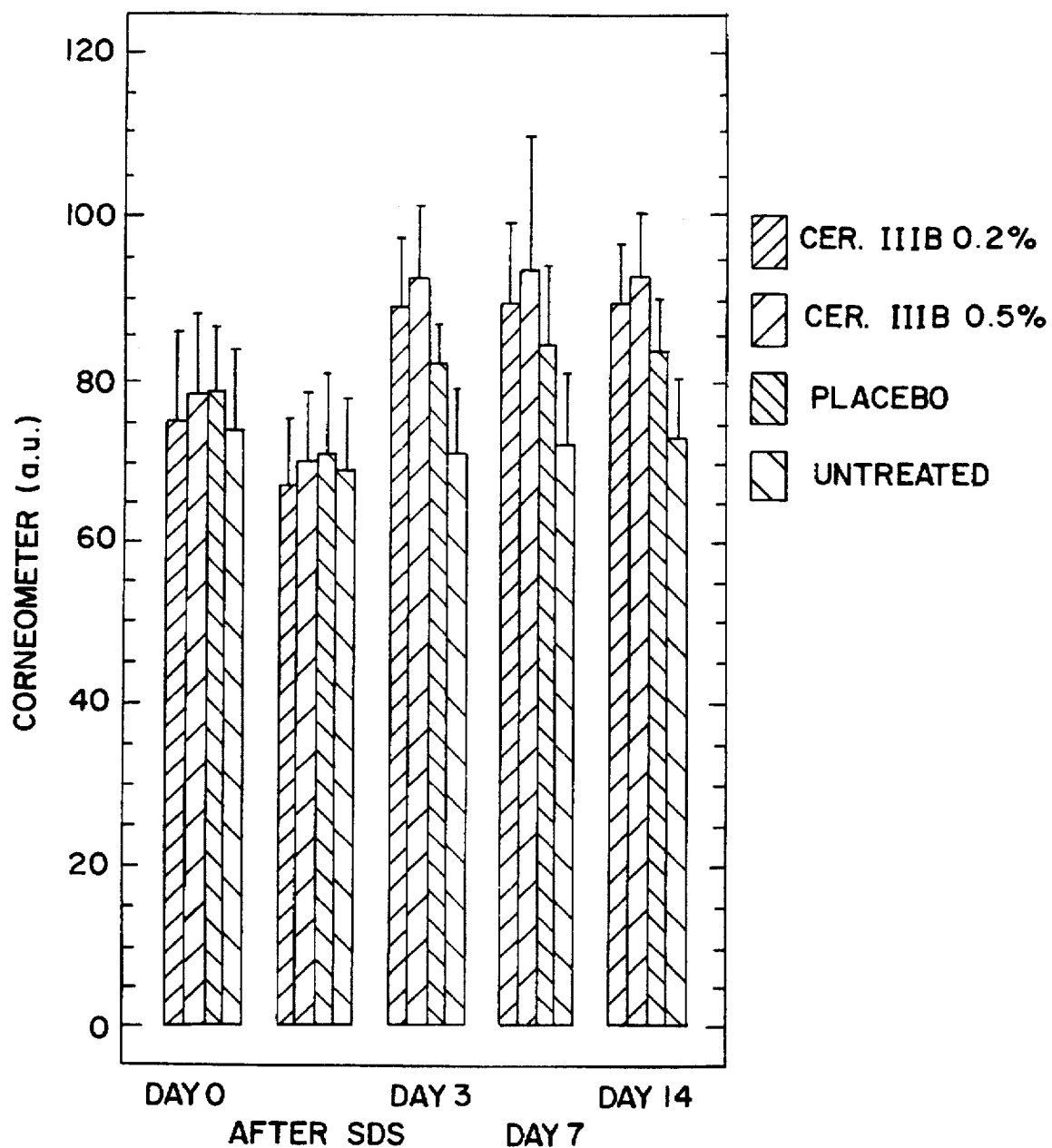
FIG. 3 shows the effects of ceramide IIIB formulations on SDS-damaged skin as measured with corneometry.
Figure 4:
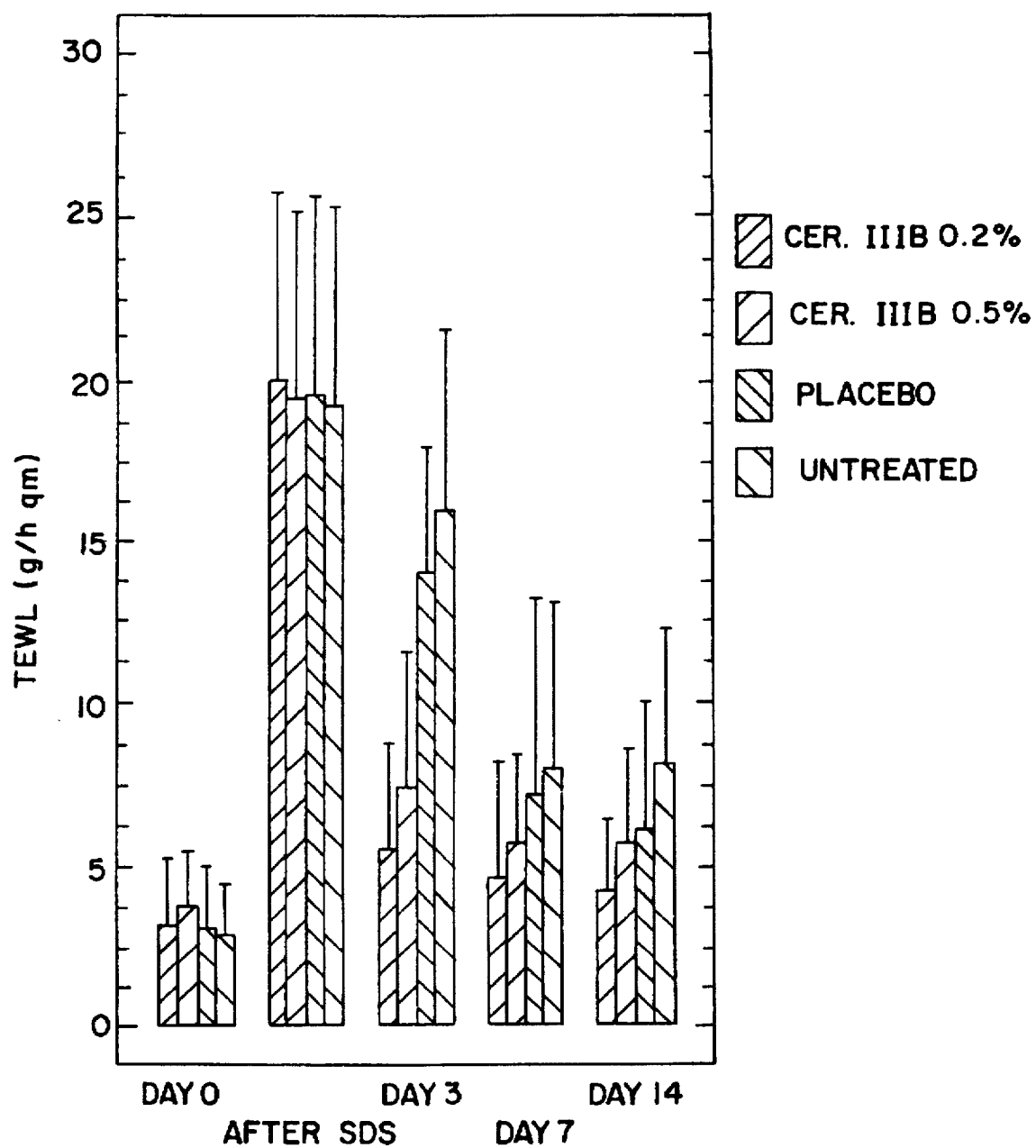
FIG. 4: as FIG. 3, as measured with TEWL.

The results of skin humidity measurements and the TEWL are shown in FIG. 3 and 4 (average plus standard deviation in barcharts).

Skin humidity: the ceramide containing creams (0.2%, 0.5%) gave clear effects compared to placebo. With two daily applications the maximal effect was achieved after around 7 days.

TEWL: The ceramide containing products normalize the TEWL in a shorter time (only three days) than the placebo product (nearly 14 days). The TEWL in the untreated area takes more than 14 days to return to normal level. Also, a clear dose-response effect can be observed with resp. 0.2 and 0.5% Ceramide IIIB.

Conclusion

A treatment period of 14 days with the ceramide containing creams produced a reduction of TEWL, accompanied with an increase of skin humidity of damaged skin compared to placebo.

Thus, the ceramide containing preparations lead to a quicker restoration of the barrier layer of SDS-damaged skin than the placebo product.

EXAMPLE 6

Role of Ceramide IIIB in Preventing Surfactant-induced Irritation of the Skin

Formulations Tested

See Example 4.

Time of Evaluation before start of treatment;
two hours after last application on day 7;
2 hours after irritation with SDS (2 h under occlusion).

Test Method

Two panels of each five female volunteers at the age of 19–55 years with healthy skin were included in the test.

Measurements were carried out at a temperature of 22°±1° C. and a relative humidity of 60±10%. Subjects were accustomed to ambient conditions for 20 min prior to any measurement. The test was carried out on the volar forearms. Initially untreated skin was measured in all four areas to find baseline values. Then the three test products were applied, one area remained untreated. The dose of application was about 2 mg/cm². In the following 7 days a home application in the morning and evening took place. Measurements were evaluated during the treatment period on day 7 two hours after the last daily application. Then the test areas on both forearms were treated with a 5% aqueous solution of sodium lauryl sulphate (SDS) and an occlusive dressing applied to induce skin irritation. The dressing was removed 2 h later, and the regions were gently washed with water and air-dried. After 1 hour the measurements were done when the level had stabilised.

Use of other cosmetic products was restricted on the test areas throughout the whole study.

Results

Figure 5:
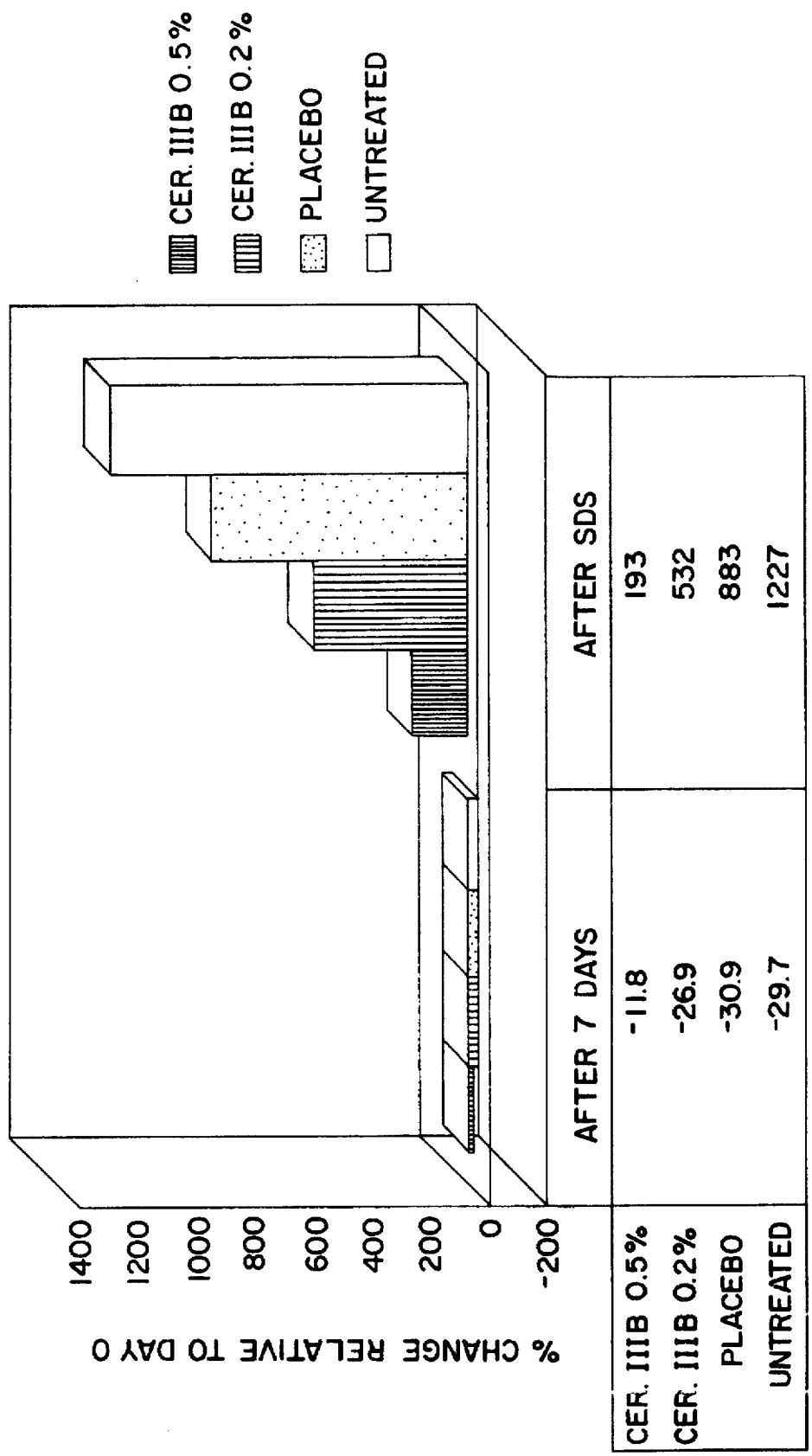
FIG. 5 shows the protective effects of ceramide IIIB formulations against SDS-challenge as measured by TEWL.
Figure 6:
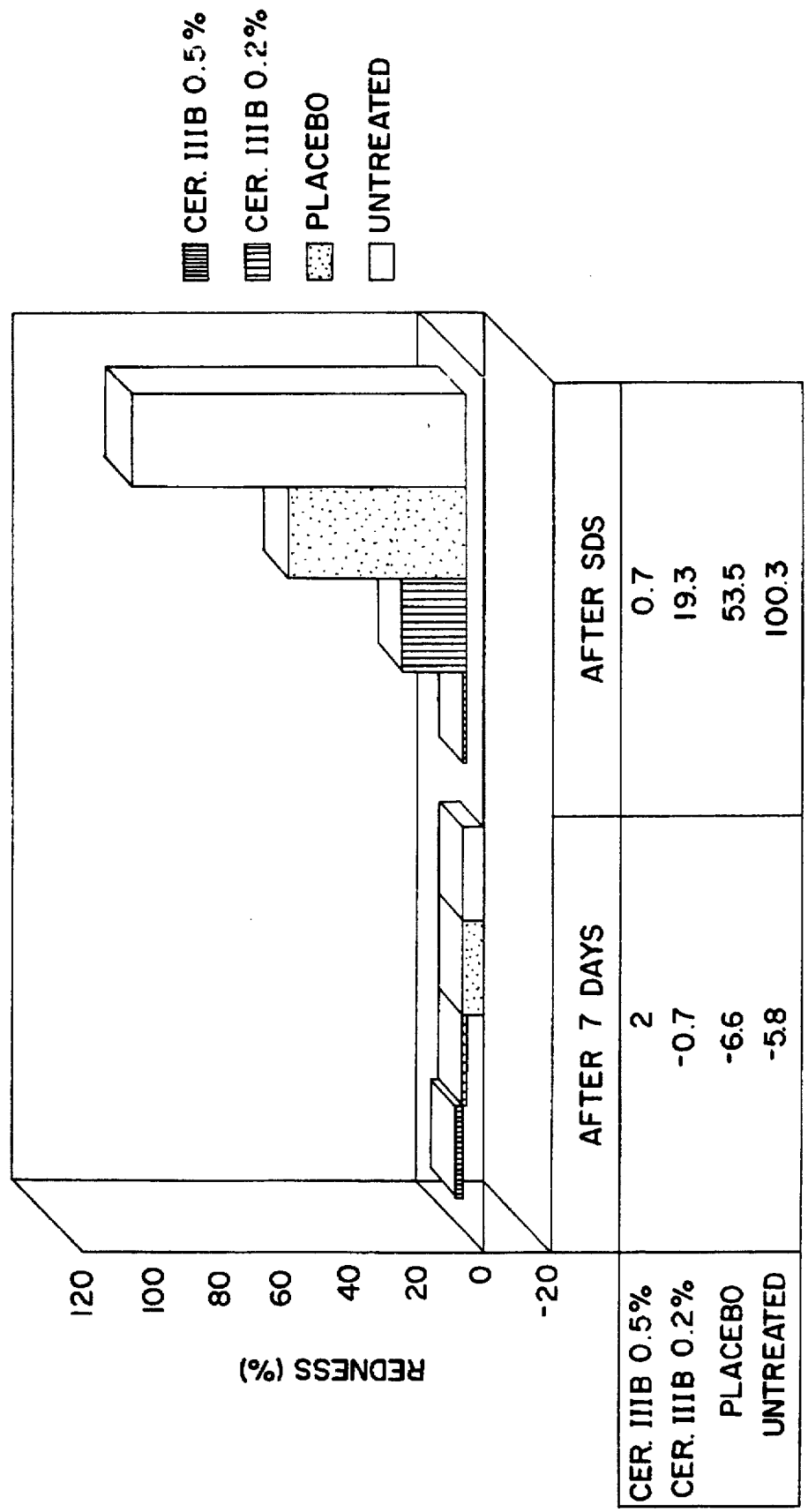
FIG. 6: as FIG. 5, as measured with chromametry.

The results of TEWL and skin colour measurements are presented in respectively FIGS. 5 and 6. Values are expressed as $(Value_{day7}-Value_{day0})/Value_{day0} \times 100\%$.

After irritation with SDS, the increase in TEWL in the areas pretreated with ceramide IIIB formulations for 7 days was much lower compared to control and placebo pretreatment. The effect was dose dependent. A similar phenomenon could be observed using skin colour as a parameter. This shows that a pretreatment with ceramide IIIB protects the skin from SDS-induced damage.

We claim:

1. A compound having the formula:

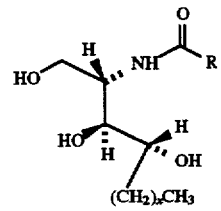

wherein R is a straight chain or branched alkyl group containing one double bond and having 2 to 55 carbon atoms and X is an integer from 11 to 21 inclusive.

2. A compound according to claim 1 which is N-oleoylphytosphingosine.

3. A method for preparing a compound according to claim 1 which comprises coupling the corresponding monounsaturated fatty acid with phytosphingosine in a solvent.

4. A method of claim 3 wherein the monounsaturated fatty acid is coupled to phytosphingosine as an activated acid.

5. A method for preparing the compound according to claim 2, which comprises coupling oleic acid to phytosphingosine in a solvent.

6. A method of claim 5 wherein oleic acid is coupled to phytosphingosine as an activated acid.

7. A pharmaceutical composition for topical application which contains the compound according to claim 1 in an amount of 0.0001% to 25% by weight of the composition.

8. A cosmetic composition for topical application which contains the compound according to claim 1 in an amount of 0.0001% to 25% by weight of the composition.

9. A pharmaceutical composition for topical application which contains the compound according to claim 2 in an amount of 0.0001% to 25% by weight of the composition.

10. A cosmetic composition for topical application which contains the compound according to claim 2 in an amount of 0.0001% to 25% by weight of the composition.

11. A method to treat mammalian skin, which method comprises topically applying a composition comprising an effective amount of the compound of claim 1.

12. The method of claim 11 wherein said composition further comprises a pharmaceutically acceptable vehicle.

13. The method of claim 11 wherein said composition further comprises a cosmetically acceptable vehicle.

14. The method of claim 11 wherein said treating results in maintaining the water characteristics of said mammalian skin.

15. The method of claim 11 wherein said treating results in restoring the water permeability characteristics of said mammalian skin.

16. A method to treat mammalian skin, which method comprises topically applying a composition comprising an effective amount of the compound of claim 2.

17. The method of claim 16 wherein said composition further comprises a pharmaceutically acceptable vehicle.

18. The method of claim 16 wherein said composition further comprises a cosmetically acceptable vehicle.

19. The method of claim 16 wherein said treating results in maintaining the water characteristics of said mammalian skin.

20. The method of claim 16 wherein said treating results in restoring the water permeability characteristics of said mammalian skin.

21. The composition of claim 7 wherein said amount is 0.005% to 5% by weight of the composition.

22. The composition of claim 21 wherein said amount is 0.01% to 2% by weight of the composition.

23. The composition of claim 8 wherein said amount is 0.005% to 5% by weight of the composition.

24. The composition of claim 23 wherein said amount is 0.01% to 2% by weight of the composition.

25. The composition of claim 12 wherein said amount is 0.005% to 5% by weight of the composition.

26. The composition of claim 25 wherein said amount is 0.01% to 2% by weight of the composition.

27. The composition of claim 13 wherein said amount is 0.005% to 5% by weight of the composition.

28. The composition of claim 27 wherein said amount is 0.01% to 2% by weight of the composition.

29. The compound of claim 1 wherein R contains 10–50 carbon atoms.

30. The compound of claim 1 wherein R contains 14–48 carbon atoms.

31. The compound of claim 1 wherein X is 13.

* * * * *